United States Patent [19]

Teng et al.

[11] 4,383,988

[45] May 17, 1983

[54] GELLED ANTIPERSPIRANT

[75] Inventors: James Teng, St. Louis; James M. Lucas, Crestwood, both of Mo.

[73] Assignee: Anheuser-Busch, Incorporated, St. Louis, Mo.

[21] Appl. No.: 103,183

[22] Filed: Dec. 13, 1979

Related U.S. Application Data

[63] Continuation of Ser. No. 900,895, Apr. 28, 1978, abandoned, which is a continuation of Ser. No. 727,004, Sep. 27, 1976, abandoned.

[51] Int. Cl.$^3$ ............................................. A61K 7/38
[52] U.S. Cl. ...................................................... 424/68
[58] Field of Search ................................... 424/68, 362

[56] References Cited

U.S. PATENT DOCUMENTS

| | | | |
|---|---|---|---|
| 2,972,545 | 2/1961 | Briskin | 424/362 X |
| 3,211,620 | 10/1965 | Henkin et al. | 424/68 |
| 3,251,824 | 5/1966 | Battista | 424/362 |
| 3,485,915 | 12/1969 | Gerstein et al. | 424/65 |
| 3,697,644 | 10/1972 | Laiderman | 424/363 |
| 3,712,886 | 11/1973 | Koyanagi et al. | 424/362 |
| 3,824,085 | 0/1974 | Teng et al. | 44/7 C |
| 3,929,986 | 12/1975 | Bouillon et al. | 424/46 |
| 3,940,384 | 0/1975 | Teng et al. | 106/170 |
| 3,953,591 | 4/1976 | Snyder | 424/365 |
| 3,957,523 | 5/1976 | Ohno et al. | 424/362 |

FOREIGN PATENT DOCUMENTS 44-48423 9/1969 Japan ................................. 424/362

*Primary Examiner*—Dale R. Ore
*Attorney, Agent, or Firm*—Gravely, Lieder & Woodruff

[57] ABSTRACT

A clear viscous and gelled antiperspirant solution comprising a gell solution of an alcoholic solvent and a gelling agent for the solvent, an antiperspirant dissolved in the gel solution, and a small but effective amount of emollient. The gelled antiperspirant can be applied easily. The antiperspirant is held effectively within the smooth film formed by the gelling agent. The gelling agent is a cellulose-based derivative modified with polyoxypropylene groups and substituted with acetyl groups.

8 Claims, No Drawings

GELLED ANTIPERSPIRANT

This is a continuation of application Ser. No. 900,895, filed Apr. 28, 1978, now abandoned, which is a continuation of abandoned application Ser. No. 727,004, filed Sept. 27, 1976, now abandoned.

BACKGROUND OF THE INVENTION

Cosmetic deodorants are preparations which mask, remove, or decrease perspiration odors, prevent their development, or do all of these. Many such products which have a satisfactory deodorant efficacy and cosmetic characteristics appear on the market each year.

In order to control objectionable odors of perspiration, it is necessary either to check the flow of excess perspiration or to eliminate its odor, or both.

A variety of substances which have astringent action inhibit the flow of perspiration. The mechanism by which such antiperspirants act has not been clearly defined.

Salts of metals such as aluminum, iron, chromium, lead, mercury, zinc, and zirconium have astringent properties which may be demonstrated by protein precipitation. However, some of these, because they produce discoloration, and others, because of possible toxic effects, are not suitable for cosmetic preparations. Salts of aluminum and zinc are those most commonly used. The astringency of these salts is also dependent on the anion. Sulfate, chloride, chlorhydroxide, and phenolsulfonate have been most widely used, although basic formate, lactate, sulfamate, and the alums are also found in antiperspirant products. Acetates are generally unsatisfactory because of odor. At the acid pH necessary for astringency, the acetic acid odor is very definite and is a difficult one to cover. Formates are to be avoided since they tend to produce skin sensitization. Aluminum salts are generally used in concentrations of 12 to 20%. Tannins and tannic acid have been used as antiperspirants.

The aluminum compound that has been most widely used in antiperspirant compositions is aluminum chlorhydroxide complex. Commonly referred to as aluminum chlorhydrate or aluminum chlorhydroxide, the product is a 5/6 basic aluminum chloride complex with the atomic ratio of aluminum to chlorine of 2:1. In dry form it is a glass-like rather than a crystalline substance, readily soluble in water. A 20% solution has a pH of approximately 4.2 with good buffering capacity. It is not irritating or sensitizing to normal skin and causes little or no damage to fabrics. The concentration recommended for use in antiperspirant products is 20%. Aluminum chlorhydrate complex is sold under a variety of trade names, dry in granular or powdered form, or as a 50% solution. The solution is stable and remains clear with little change in pH over long periods of standing. The solid is insoluble in 95% ethyl alcohol, but the 50% solution is miscible in all proportions with 95% ethyl alcohol. (S. Plechner, Cosmetics: Science and Technology, Vol. 2, Balsam et al Ed, John Wiley & Sons, Inc., 1972, p. 375).

Antiperspirants appear in several physical forms. The most popular forms are creams, lotions, sticks, powders, and liquids.

Clear roll-on lotions may be prepared using an aqueous alcohol solution of such thickeners as methyl cellulose or hydroxyethyl cellulose in a concentration of 0.4 to 0.7% with aluminum chlorhydroxide 18 to 20%. S.D. 40 alcohol may be used at 15 to 20%. Addition of small amounts of humectant and emollient prevents formation of aluminum salt crystals on the ball and improves the feel of the product on the skin. A nonionic emulsifier will be needed to disperse the perfume.

The final viscosity of a roll-on-type product should be established before a package is selected. The amount of clearance between the ball and fitment will depend on the viscosity of the product. If the lotion is too thin, it will drip and run as it is applied. If it is too thick, it will be scraped off on the fitment as the ball turns and will feel wet after application. The exact viscosity desired and the amount to be applied will vary with the kind of thickener used in the lotion and with the astringent selected. (Plechner, p. 391).

Antiperspirants have also been developed in stick form. A type of antiperspirant stick is made from a solidified alcohol gel composition. A combination of an astringent chloride with a hard wax dissolved by heating in alcohol will form a solid gel on cooling. Addition of a higher fatty acid or an ester improves the texture and rigidity of the product. (Plechner, p. 392).

Patent literature reveals an antiperspirant stick comprising a sodium stearate-aqueous alcohol gel base with sodium zirconium lactate as the antiperspirant agent.

Patent literature further reveals an alcohol-sodium stearate gel antiperspirant stick containing aluminum hydroxide as the active antiperspirant agent. The use of isopropyl palmitate or isopropyl myristate as a physical stabilizer is also revealed. (Plechner, p. 394).

The soap-gel sticks in general are not as effective as a well-formulated antiperspirant cream or lotion. However, they have reasonably good astringency and constitute a convenient form of application.

It is an object of this invention to provide a gelled antiperspirant which will keep the active ingredient in uniform suspension. It is a further object to provide a gelled antiperspirant with a suitable dispensing viscosity for roll-on application. It is still a further object to provide a gelled antiperspirant that holds the active ingredient in a residual film on the skin and has a longer lasting effect.

SUMMARY OF THE INVENTION

This invention involves a gelled antiperspirant comprising a solvent, an antiperspirant, and a gelling agent. The antiperspirant is held effectively within the smooth film formed by the gelling agent. The gelling agent is a cellulose-based derivative modified with polyoxypropylene groups and substituted acetyl groups.

DETAILED DESCRIPTION

The antiperspirant gel of the present invention comprises a solvent, an antiperspirant, an emollient, and a gelling agent.

The solvent is an alcohol. Suitable solvents are isopropyl alcohol, and ethyl alcohol. About 45% (w/w) to about 80% (w/w) solvent is used in the formulation.

The antiperspirant is an aluminum salt. Suitable antiperspirants are aqueous aluminum chlorhydrate, and aluminum chlorhydrate alcohol soluble complex. About 14% (w/w) to about 40% (w/w) antiperspirant is used in the formulation.

Teng et al, U.S. Pat. No. 3,824,085 discloses the gelling agents to be used in this invention. Basically, the gelling agent is a polymeric carbohydrate derivative selected from the group consisting of hydroxypropyl cellulose esters and hydroxypropyl starch esters and mixtures of these esters. These esters can have a D.S. of about 1.2 to about 3 and a M.S. of hydroxypropyl groups of about 2 to about 8. Suitable esters are:

hydroxypropyl cellulose acetate
hydroxypropyl starch acetate

Teng et al, U.S. Pat. No. 3,940,384 discloses another gelling agent which can be used in this invention. This gelling agent is methyl hydroxypropyl cellulose acetate. This ester has a D.S. of acetyl groups of about 0.8 to about 2.5 and a M.S. of hydroxypropyl groups of about 2 to about 8. The D.S. of methyl groups is about 0.1 to about 1.0.

The gelling agent can make up from about 0.6% to about 2.0% by weight of the antiperspirant solution.

The important physical properties of the gelling agent are summarized in Table 1. The usual form is that of a white powder of 20–40 mesh. Depending upon the equipment, the particle size can be varied. The material is basically not hygroscopic and therefore has low moisture content.

The gelling agents are highly substituted derivatives and are generally inert to enzymatic activity.

TABLE 1

Physical Properties of Gelling Agent

| Color | White |
|---|---|
| Physical form | Soft powder, 20–40 mesh |
| Moisture | 0.5% |
| Ash | 1.0% |
| Specific Gravity | 1.017 |
| Glass Transition Temperature | 85° C. |
| Melting Range | 190–210° C. |
| Char Point | 240° C. |
| Biological Activity | Does not support microbial growth. Inert to proteolytic amylolytic degradation. |

The formulation is prepared by first gelling the alcohol solvent with the gelling agent. Then the 50% (w/w) aqueous aluminum chlorohydrate is added slowly while the gelled solution is agitated rapidly. Finally the emollient (dibutyl phthalate) is added. The gelled solution is viscous and clear, but pourable.

Additives, such as perfume and additional emollients, can also be incorporated into the composition.

EXAMPLE I

The following ingredients in the respective amounts shown were used to prepare an antiperspirant gel:

| Ingredient | Percent By Weight |
|---|---|
| Dibutyl phthalate | 1.0 |
| Isopropyl alcohol | 53.9 |
| Aluminum chlorohydrate (50% aqueous solution) | 44.0 |
| Hydroxypropyl cellulose acetate | 1.1 |
| D.S. 1.33 | |
| M.S. 4.00 | |

The mixture was prepared by mixing 1.1 gm hydroxypropyl cellulose acetate with 68.6 ml isopropyl alcohol. 44.0 gm of 50% aqueous solution of aluminum chlorohydrate was slowly added to the gel solution while it was agitated rapidly. 1.0 gm dibutyl phthalate was then added to the solution. The gelled solution was clear and viscous, but was pourable.

EXAMPLE II

The following ingredients in the respective amounts shown were used to prepare an antiperspirant gel:

| Ingredient | Percent By Weight |
|---|---|
| Dibutyl phthalate | 10.0 |
| Ethyl alcohol | 49.0 |
| Aluminum chlorohydrate (50% aqueous solution) (Chlorohydrol from Reheis Chemical Co., Chicago, Illinois) | 40.0 |
| Hydroxypropyl cellulose acetate | 1.0 |
| D.S. 0.44 | |
| M.S. 4.00 | |

The mixture was prepared as in Example I.

EXAMPLE III

The following ingredients in the respective amounts shown were used to prepare an antiperspirant gel:

| Ingredient | Percent By Weight |
|---|---|
| Lauryl lactate | 2.0 |
| Ethyl alcohol (95% S.D. 40) | 81.8 |
| Aluminum chlorohydrate (Alcohol Soluble) (Rehydrol from Reheis Chemical Co., Chicago, Ill. or Wickenol 363 D from Wickhen Products Inc., Belleville, New Jersey) | 14.6 |
| Perfume | 0.8 |
| Hydroxypropyl cellulose acetate | 0.8 |
| D.S. 1.5 | |
| M.S. 4.0 | |

The mixture was prepared as in Example I, with the exception that the aluminum chlorohydrate was added very slowly, and the stirring step required 20 hours.

What is claimed is:

1. A clear, viscous and pourable gelled antiperspirant solution capable of forming a residual film on the skin of the user, said film holding the active ingredient to the skin, said solution consisting essentially of (a) a gel solution which is alcohol and a water insoluble gelling agent for said alcohol, said alcohol being present in amount of about 45 to about 80% by weight of the antiperspirant solution and said gelling agent comprising about 0.6% to about 2.0% by weight of the antiperspirant solution, said gelling agent being selected from the group consisting of hydroxypropyl cellulose esters, hydroxypropyl starch esters, and mixtures thereof, said esters having a degree of substitution of about 1.2 to about 3 and a degree of molar substitution of hydroxypropyl groups of about 2 to about 8, (b) an antiperspirant dissolved in said gel solution to yield the gelled antiperspirant solution, said antiperspirant being present in amount of about 40 to about 14% by weight of the antiperspirant solution, and (c) an emollient.

2. The product of claim 1 wherein the gelling agent is hydroxypropyl cellulose acetate.

3. The product of claim 1 wherein the gelling agent is hydroxypropyl starch acetate.

4. The product of claim 1 wherein the antiperspirant is alcohol soluble aluminum chlorohydrate.

5. The product of claim 1 wherein the antiperspirant is an aqueous solution of aluminum chlorohydrate.

6. A clear, viscous and pourable gelled antiperspirant solution capable of forming a residual film on the skin of the user, said film holding the active ingredient to the skin, said solution consisting essentially of (a) a gel solution which is alcohol and a water insoluble gelling agent which is methyl hydroxypropyl cellulose acetate having a degree of molar substitution of hydroxypropyl groups of about 2 to about 8, a degree of substitution of methyl groups of about 0.1 to about 1, and a degree of substitution of acetyl groups of about 0.8 to about 2.5, said alcohol being present in amount of about 45 to about 80% by weight of the antiperspirant solution and said gelling agent being present in amount of about 0.6 to about 2.0% by weight of the antiperspirant solution, (b) an antiperspirant dissolved in said gel solution to yield the gelled antiperspirant solution, said antiperspirant being present in amount of about 40 to about 14% by weight of the antiperspirant solution, and (c) an emollient.

7. The product of claim 6 wherein the antiperspirant is alcohol soluble alluminum chlorohydrate.

8. The product of claim 6 wherein the antiperspirant is an aqueous solution of aluminum chlorohydrate.